(12) United States Patent
Speck et al.

(10) Patent No.: US 9,746,540 B2
(45) Date of Patent: Aug. 29, 2017

(54) DEVICE AND METHOD FOR CALIBRATING TRACKING SYSTEMS IN IMAGING SYSTEMS

(71) Applicant: Albert-Ludwigs-Universitaet Freiburg, Freiburg (DE)

(72) Inventors: Oliver Speck, Magdeburg (DE); Ilia Kadachevitch, Hermsdorf (DE); Thomas Ernst, Honolulu, HI (US); Maxim Zaitsev, Freiburg (DE); Crispin Lovell-Smith, Freiburg (DE); Julian Maclaren, Freiburg (DE)

(73) Assignee: ALBERT-LUDWIGS-UNIVERSITAET FREIBURG, Freiburg (DE)

( * ) Notice: Subject to any disclaimer, the term of this patent is extended or adjusted under 35 U.S.C. 154(b) by 11 days.

(21) Appl. No.: 14/440,599

(22) PCT Filed: Nov. 6, 2013

(86) PCT No.: PCT/EP2013/073169
§ 371 (c)(1),
(2) Date: Aug. 5, 2015

(87) PCT Pub. No.: WO2014/072343
PCT Pub. Date: May 15, 2014

(65) Prior Publication Data
US 2015/0331078 A1    Nov. 19, 2015

(30) Foreign Application Priority Data
Nov. 6, 2012 (DE) .................. 10 2012 021 623

(51) Int. Cl.
*G06K 9/00* (2006.01)
*G01R 33/567* (2006.01)
(Continued)

(52) U.S. Cl.
CPC .......... *G01R 33/5673* (2013.01); *A61B 5/055* (2013.01); *A61B 6/03* (2013.01);
(Continued)

(58) Field of Classification Search
None
See application file for complete search history.

(56) References Cited

U.S. PATENT DOCUMENTS 5,389,101 A * 2/1995 Heilbrun .................. A61B 5/06
                                                        348/E13.014
6,377,906 B1 * 4/2002 Rowe ..................... G01C 21/16
                                                        244/164
(Continued)

FOREIGN PATENT DOCUMENTS

CA  WO 2007014470 A2 *  2/2007  ............. G01B 7/008
EP        1 913 333       4/2008
(Continued)

OTHER PUBLICATIONS

Daniilidis ("Hand Eye Calibration Using Dual Quaternions", 1999).*
(Continued)

*Primary Examiner* — Avinash Yentrapati
(74) *Attorney, Agent, or Firm* — Paul Vincent

(57) ABSTRACT

A device and a method for calibrating the coordinate system of imaging systems having a tracking system prior or during image data acquisition, e.g. by way of magnetic resonance tomography.

14 Claims, 2 Drawing Sheets

(51) Int. Cl.
  *G01R 33/58* (2006.01)
  *G01T 1/161* (2006.01)
  *A61B 5/055* (2006.01)
  *A61B 6/03* (2006.01)
  *A61B 6/00* (2006.01)
  *G01R 33/28* (2006.01)
  *G01R 33/565* (2006.01)
  *A61B 34/20* (2016.01)

(52) U.S. Cl.
  CPC .............. *A61B 6/582* (2013.01); *G01R 33/28* (2013.01); *G01R 33/56509* (2013.01); *G01R 33/58* (2013.01); *G01T 1/161* (2013.01); *A61B 34/20* (2016.02); *F04C 2270/041* (2013.01)

(56) References Cited

U.S. PATENT DOCUMENTS

| | | | | |
|---|---|---|---|---|
| 7,089,148 | B1* | 8/2006 | Bachmann | A61B 5/1114 600/595 |
| 8,121,361 | B2* | 2/2012 | Ernst | A61B 5/055 382/103 |
| 2001/0053204 | A1* | 12/2001 | Navab | A61B 6/547 378/205 |
| 2002/0044631 | A1* | 4/2002 | Graumann | A61B 6/547 378/205 |
| 2002/0070818 | A1* | 6/2002 | Kim | H04N 19/503 332/106 |
| 2003/0182072 | A1* | 9/2003 | Satoh | G06T 7/0018 702/95 |
| 2004/0015075 | A1* | 1/2004 | Kimchy | G01T 1/161 600/424 |
| 2005/0137475 | A1* | 6/2005 | Dold | A61B 5/055 600/414 |
| 2006/0262961 | A1* | 11/2006 | Holsing | G06T 7/0018 382/103 |
| 2007/0034731 | A1* | 2/2007 | Falco | G01B 7/008 244/3.1 |
| 2007/0216675 | A1* | 9/2007 | Sun | G06T 11/00 345/419 |
| 2007/0280508 | A1* | 12/2007 | Ernst | A61B 5/055 382/107 |
| 2008/0144773 | A1* | 6/2008 | Bar-Zohar | A61B 1/00096 378/98.12 |
| 2008/0219405 | A1* | 9/2008 | Falco | A61N 5/1049 378/65 |
| 2009/0041323 | A1* | 2/2009 | Lachaine | A61B 8/483 382/131 |
| 2011/0193883 | A1* | 8/2011 | Palais | G06T 13/20 345/655 |
| 2014/0241497 | A1* | 8/2014 | Keall | G06T 7/0028 378/62 |

FOREIGN PATENT DOCUMENTS

| | | | | |
|---|---|---|---|---|
| JP | WO 2007037307 | A1 * | 4/2007 | A61B 6/032 |
| WO | WO 2007/037307 | | 4/2007 | |

OTHER PUBLICATIONS

Stefan Thesen et al., "Prospective Acquisition . . . " Magnetic Resonance in Medicine 44:457-465 (2000).
André J.W. Van Der Kouwe et al., "Real-TIme Rigid . . . " Magnetic Resonance in Medicine 56:1019-1032 (2006).
Melvyn B. Ooi et al., "Prospective Real-Time . . . ", Magnetic Resonance in Medicine 62:943-954 (2009).
Dold C. et al., "Prospective head motion . . . ", Med Image ComputAssist Interv 2005;8 (Pt1):482-489.
M. Zaitsev et al., "Magnetic resonance imaging . . . ", Neuro Image 31 (2006) 1038-1050.
Lei Qin et al., "Prospective Head-Movement . . . ", Magnetic Resonance in Medicine 62:924-934 (2009).
Brian C. Andrews-Shigaki et al., "Prospective Motion Correction . . . ", Journal of magnetic resonance imaging 33:498-504 (2011).
Murat Aksoy et al., "Real-Time Optical . . . ", Magnetic Resonance in Medicine 66:366-378 (2011).
Forman C. et al., "Self-encoded marker . . . ", Med Image Comput Comput Assist Interv 2010;13 (Pt1): 259-266.
Murat Aksoy et al., "Hybrid Prospective . . . ", Magnetic Resonance in Medicine 67:1237-1251 (2012).
Rainer Boegle et al., "Combining prospective motion . . . ", Magn Reson Mater Phy (2010) 23:263-273.
Kadashevich D. et al., "Automatic motion selection . . . ", Proceedings of 28th Annual Scientific meeting of ESMRMB 2011. DOI:10.1007/s10334-011-0269.
Hamilton, William Rowan et al., "On quaternions, . . . ", Philosophical Magazine, vol. 25, pp. 489-495, 1844.

* cited by examiner

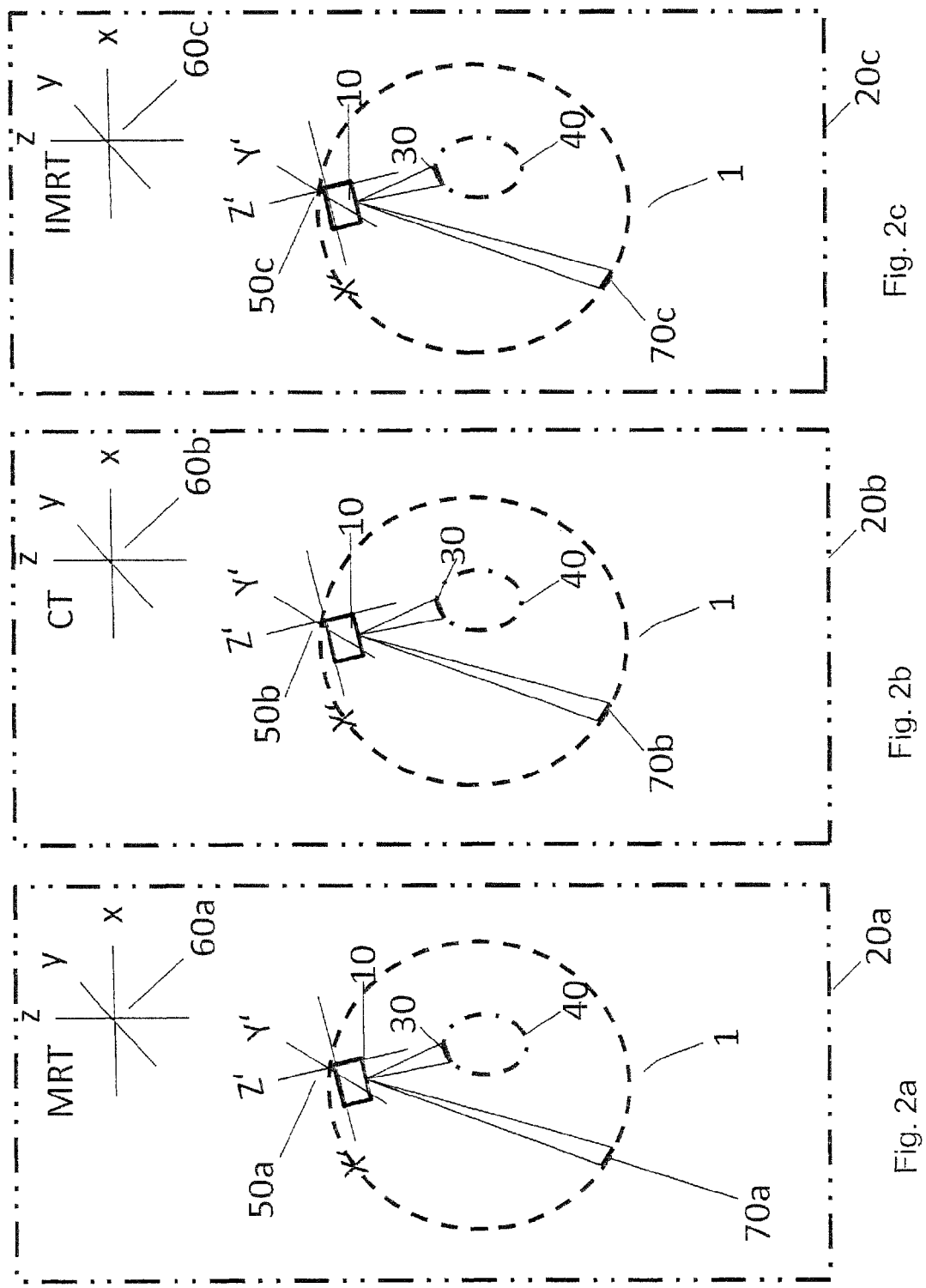

DEVICE AND METHOD FOR CALIBRATING TRACKING SYSTEMS IN IMAGING SYSTEMS

This application is the national stage of PCT/EP2013/073169, filed Nov. 6, 2013 and also claims Paris convention priority from DE 10 2012 021 623.9, filed Nov. 6, 2012.

BACKGROUND OF THE INVENTION

The invention concerns a device and a method for calibrating coordinate systems of imaging systems with a tracking system prior to or during image data acquisition, e.g. by means of magnetic resonance tomography.

Modern medical or biomedical imaging methods provide detailed images of living organisms. Such methods include i.a. magnetic resonance tomography MRT, computer tomography CT and nuclear medical imaging, such as e.g. positron emission tomography (PET), single photon emitted computer tomography (SPECT) or intensity-modulated radiation therapy (IMRT).

A large number of these methods require long measurement times of many seconds or minutes and are therefore prone to image quality losses due to movement of the measurement object, a patient or an animal, which could render the recordings useless in that so-called "blurred recordings" are produced.

Methods for reducing or eliminating these aberrations caused by movement of the object are e.g. prospective or retrospective motion correction, in which the movement of the measurement object is either already compensated for during recording by means of suitable tracking of the measuring field or during image reconstruction. For this reason, even in case of movement during the measurement, the generated images do not show any corresponding aberrations, as described in citations 1-11.

The movement information may thereby either be measured by means of the imaging modality itself, often referred to e.g. as "navigators". However, in most cases this requires an extension or disturbance of the measurement.

Alternatively, the movement information may e.g. be optically detected by a position measurement system or also a tracking system, thereby performing the imaging method itself without disturbance. One necessary step in case of position detection using a system of this type is the calibration of the coordinate systems between the imaging system and the position measurement system, also called tracking system. In this case, the spatial transformation (translation and rotation with a total of six degrees of freedom) between the two modalities must be exactly determined as described in citations 5 and 12.

EP 1 913 333 B1 discloses a device and a method for detecting a drift in calibrated tracking systems for medical applications in order to be able to localize features with respect to one or more coordinate systems within a reference coordinate system using a calibrated tracking system to which a motion sensor is mounted for detecting movements of the tracking system. When such a movement is detected, the tracking system is re-calibrated.

The common methods for calibrating the coordinate systems of tracking systems and imaging systems include measurement of a known object, which is visible for both methods, by both systems, both the imaging modality and the tracking system, either in only one position or in different object positions. The calibration accuracy that can be achieved in this connection depends on the measurement accuracy of both systems and the number of measurements. Due to the fact that one system and in this case usually the imaging system, shows the greater measurement errors and is substantially slower, the accuracy of the procedure is limited and calibration may be time-consuming (minutes to hours).

The problems of these common methods are therefore:
1) For high accuracy, the measurements must be performed in several positions with high measurement accuracy, i.e. with respect to the spatial resolution of the imaging modality, and therefore require long measurement times.
2) The calibration accuracy is limited by measurement errors of both systems e.g. by errors in the reproduction accuracy of the imaging modality.
3) Calibration may be very time-consuming and may take up to several hours.
4) When the systems are changed, re-calibration requires renewed performance of all measurements with the full expenditure of time. Undesired calibration changes may also result from slow instabilities, so-called drifts, in the measurement system.
5) The transfer of the calibration between different imaging modalities and therapy modalities e.g. for radiation therapy, again requires the full calibration effort for each imaging modality.

In view of the above, it is the object of the present invention to obtain fast and precise calibration of the coordinate systems of imaging systems and tracking systems without having to measure an object, which can be detected by both systems, in one or more positions.

A further object of the present invention consists in avoiding useless recordings due to object movements during imaging. It would furthermore be desirable to enable combination of several imaging modalities for detecting objects without increasing the calibration expense.

SUMMARY OF THE INVENTION

This object is achieved by a device and method in accordance with the independent claims as well as the further advantageous embodiments in accordance with the dependent claims.

Proposed is a device for calibrating tracking systems in imaging systems, e.g. for MRT or IMRT or CT, comprising at least:
  a tracking system with a coordinate system,
  at least one imaging system, and
  at least one first marker that is arranged as a reference marker stationarily relative to the imaging system, and the position and orientation of which are calibrated in a coordinate system of the imaging system.

The device comprises at least one tracking system which detects the position of one or more markers, characterized by six degrees of freedom for rotation and translation, once or repeatedly.

The location of the reference marker relative to the imaging instrument is known from a pre-calibration. If, e.g. a camera system is mounted to a wall or the ceiling of a room or is designed as a mobile tracking system, as it is the case in many applications, the tracking system can be re-calibrated within seconds by means of the inventive fixed marker. In contrast to the method of EP 1 913 333 B1, the present invention enables repeated absolute calibration by means of the first marker that is used as an external marker or reference marker in order to calibrate the tracking system, wherein the tracking system is not calibrated to the first coordinate system. For this reason, the tracking system can be calibrated by the calibrated marker with one position recording in less than 1 second.

In addition to fast calibration of the tracking system, permanent re-calibration of the tracking system during the imaging proceedings is moreover also possible due to the calibrated marker.

In one embodiment of the invention, the first marker cooperates with the tracking system in such a fashion that a changing position of the tracking system during imaging can be detected via the tracking system by means of the first marker and the tracking system can be re-calibrated.

In a further embodiment of the invention, the tracking system may be arranged outside or, in particular, also within the imaging system. It may be arranged permanently or also temporarily, i.e. in a removable fashion. In this case, repeated calibration or also re-calibration would be necessary.

In a further embodiment of the invention, the tracking system may be arranged outside of the imaging system.

At least one of these first markers is a permanent stationary reference point that is mounted and arranged within the imaging system. One or more of these first markers may also be arranged outside of one or more imaging systems.

The first marker may also be arranged outside of the imaging system.

Stationary with respect to the marker thereby refers to the stationary mounting of the marker relative to the imaging system. This marker is calibrated by single exact determination of its position and orientation in the coordinate system of the imaging modality, via a so-called cross calibration.

Further markers may be mounted to movable objects within the imaging system.

In accordance therewith, in a further development of the invention, at least one second marker is provided to be arranged on a movable object such that the position and the orientation of the marker in the coordinate system of the tracking system can be detected during imaging and can be transferred to the coordinate system of the imaging system. This enables tracking of the orientation and position of image recording in a continuous fashion or in regular intervals during imaging such that the imaging volume remains stationary with respect to the moved measurement object. This reduces or eliminates aberrations due to movement of the object.

In one advantageous embodiment of the invention, each of a plurality of markers is arranged in imaging systems such that their position and orientation in the coordinate system of the respective imaging system are calibrated, wherein the position and orientation of the marker arranged on the movable object can be transferred from the coordinate system of the imaging system to the coordinate systems of the imaging systems through measurement of the position and orientation by means of the tracking system.

This device and this method enable automatic transfer of recording positions from one imaging modality to another without having to record the orientation. This enables image recordings e.g. of patients or test animals in an exactly identical position and section orientation between different imaging modalities and can reduce the duration of the examination or reduce the radiation exposure. This also enables transfer of e.g. the coordinates of an image point that was detected in an imaging modality such as e.g. the position of a tumor or another lesion to therapy systems e.g. a radiation device. Up to now, external fixations have been frequently used that force the patient into a predetermined position. With this, recordings of several imaging modalities can furthermore be made to coincide in order to represent the results simultaneously and spatially correctly superimposed. This enables combination of different information of different imaging systems for diagnostics as well as utilization of the information of an imaging modality for performing interventions during imaging on a different modality. In this fashion, it would be possible to measure e.g. target regions for an intervention from a purely diagnostic imaging modality, e.g. tumors, by means of MRT, and transfer them to an interventional imaging modality such as e.g. intraoperative X-ray or angiography in order to support the intervention.

The dynamic position of these objects is detected by the tracking system in its internal coordinate system and can e.g. be used for correcting object movements during image recording. Fast calibration of the tracking system is possible with one single measurement of the position of the stationary marker with the tracking system. The position of the tracking system in the coordinates of the imaging system can be determined from the coordinates of the marker in the coordinates of the tracking system and the knowledge of the position of the stationary marker in the coordinates of the imaging system. Since the position measurement system is generally much faster and more accurate than the imaging modality or also the imaging system, this enables highly precise re-calibration that is also extremely fast in case of several measurements.

In accordance with a further embodiment of the invention, there is a method for calibration of tracking systems in imaging systems, e.g. for MRT or IMRT or CT comprising at least the following steps:

providing a tracking system with a coordinate system and at least
one imaging system,
providing at least one first marker that is arranged as a reference marker stationarily relative to the imaging system and the position and orientation of which have been calibrated in a coordinate system of the imaging system.

In a further development of the method, the marker cooperates with the tracking system in such a fashion that the tracking system detects a changing position of the tracking system during imaging via the first marker and the tracking system is re-calibrated.

In one embodiment, calibration may be performed as a one-time calibration in the form of a cross calibration of the coordinate system of the tracking system with the coordinates $c_0$, C, wherein $c_0$ is the translation quaternion and C the rotation quaternion, wherein the position and orientation $r_0$, R of the first marker in the coordinate system of the tracking system are stored and the current position and orientation $x_0$, X of the reference point in the coordinate system of the tracking system are used for calibration in order to calculate the current cross calibration $s_0$, S as follows:

$$S=X^**RC$$

wherein $X^*$ is the conjugated rotation quaternion of the quaternion X and $$s_0=c_0+C^r_0C-S^x_0S$$

wherein $C^*$ and $S^*$ are the conjugates of the rotation quaternions C and S.

In a first variant of this method, the stationary reference point is also used during the measurement by means of the imaging modality, during which the changing position of a further marker on the imaging object is detected in order to dynamically monitor or correct calibration. This enables detection and compensation of temporal instabilities or drifts in the position measurement system. It therefore provides dynamic re-calibration of the coordinate systems. Assuming that the reference marker is stationary, an apparent movement is caused by these temporal instabilities and can be used for correction.

For correcting the drift, the initial positions (translation quaternion) and orientations (rotation quaternion) of the object $t_0$, $T_0$ and reference marker $d_0$, $D_0$ are measured. The geometric transformation between these two $x_0$, $X_0$ is therefore:

$$X = D^*_0 T_0 \text{ and } x_0 = t_0 - X^* d_0 X$$

If $t_1$, $T_j$ and $d_j$, $D_j$ are the current tracking data at the point in time j, the corrected object position $t_{j\ corr}$, $T_{j\ corr}$ can be calculated as:

$$T_{j\ corr} = D_j D^*_0 T_j \text{ and } t_{j\ corr} = t_j - T^*_{j\ corr} X^* (d_0 - d_j) \times T_{j corr}$$

In one further embodiment of the invention this "drift correction" is performed by mounting the reference marker at a stationary point (mechanically) independently of the imaging modality. This enables detection and compensation of even the smallest movements of the imaging system. Such movements, e.g. vibrations may be generated e.g. in magnetic resonance tomography in measurements with very strong gradient switching e.g. in diffusion measurements. The dynamic re-calibration is performed analogously to the previous variants.

In one alternative embodiment variant, this dynamic correction is performed in that the reference marker is mounted to the imaging modality and the tracking system is stationarily mounted (mechanically) independently of the imaging modality. This also allows detection of possible mechanical movement of the imaging system.

In a further method variant, several such stationary markers are mounted in different imaging modalities and are exactly calibrated once, i.e. are calibrated relative to the coordinate system of the imaging modality.

In accordance therewith, in this embodiment of the invention, each of a plurality of markers is arranged in the imaging systems such that their position and orientation in the coordinate system of the respective imaging system has been calibrated, wherein the position and orientation of the marker arranged on the movable object are converted from the coordinate system of the imaging system into the coordinate systems of the imaging systems.

By using these reference markers, examinations of the same object or the same patients on a plurality of devices or imaging systems or imaging modalities can be made to exactly coincide.

In a further development of the method, at least one second marker is arranged on a movable object such that the position and orientation of the marker in the coordinate system of the tracking system is detected during imaging and is converted into the coordinate system of the imaging system.

This enables tracking of the orientation and position of the image recording on a continuous basis or at regular intervals during imaging such that the imaging volume remains stationary with respect to the moved measurement object. This reduces or eliminates aberrations caused by movement of the object.

The figures below exemplarily illustrate and describe in more detail embodiments of the invention, wherein the invention is not limited to these.

BRIEF DESCRIPTION OF THE DRAWING

FIGS. 2a, 2b and 2c schematically show an arrangement of a plurality of imaging systems with associated coordinate systems.

DESCRIPTION OF THE PREFERRED EMBODIMENT

Figure 1:
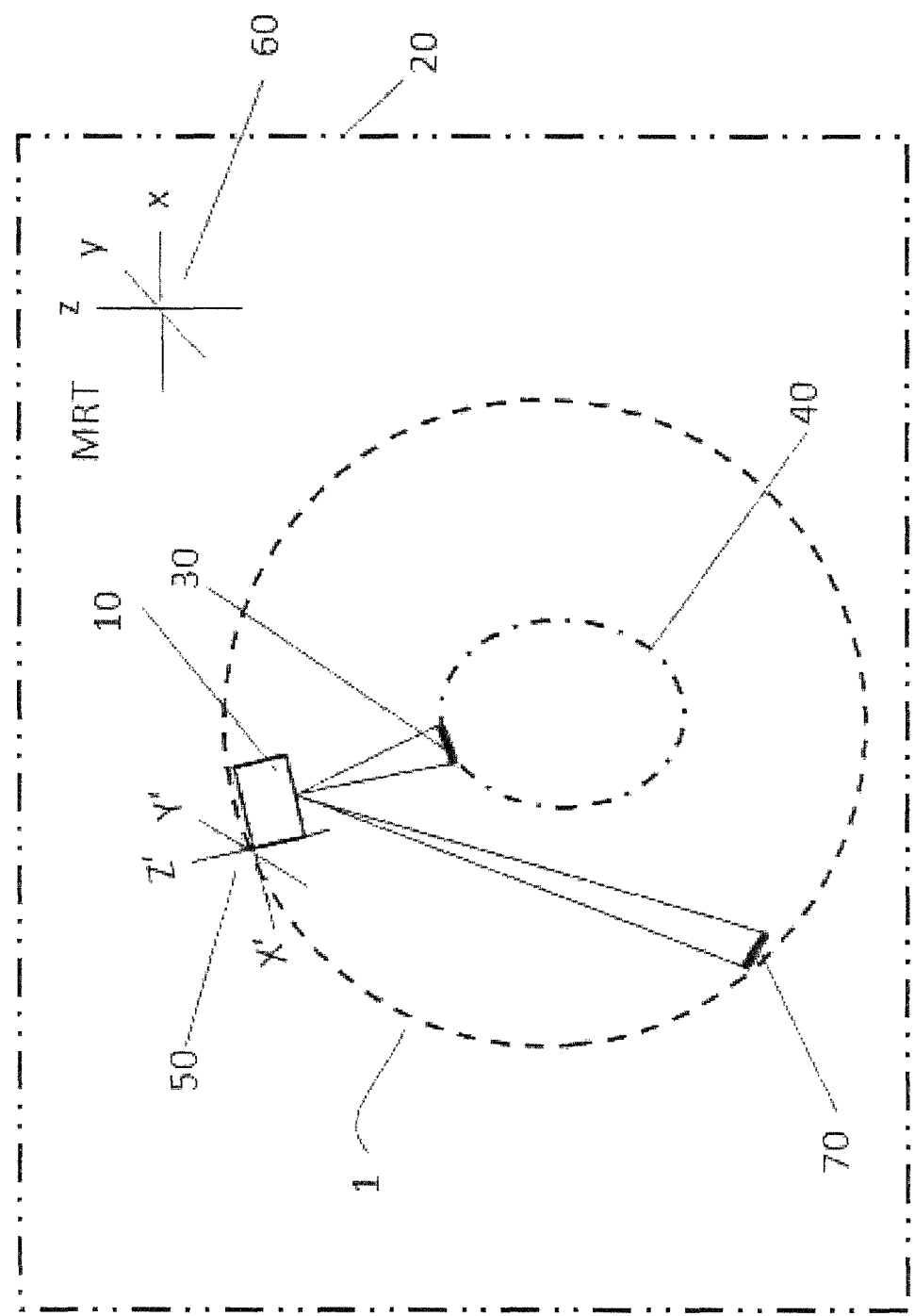
FIG. 1 schematically shows an arrangement of a device 1 for calibrating a tracking system in an imaging system.

The reference numerals of corresponding elements in the figures are identical.

In accordance with FIG. 1, the schematically illustrated device 1 comprises a tracking system 10 which is arranged in an imaging system 20 e.g. for MRT. The tracking system 10 has a coordinate system 50. The device moreover has a first marker 70 which is stationary relative to the imaging system 20 as a reference marker and the position and orientation of which are calibrated in a coordinate system 60 of the imaging system 20.

The tracking system 10 and the first marker 70 are arranged within the imaging system 20.

A second marker 30 is provided on a movable object 40 such that the position and orientation of the marker 30 can be detected in the coordinate system 50 of the tracking system 10 during imaging and can be transferred to the coordinate system 60 of the imaging system 20.

In principle, the device 1 for calibrating tracking systems 10 in imaging systems 20a, 20b, 20c, e.g. for MRT or IMRT or CT, may comprise at least the following components:
a tracking system 10 with a coordinate system 50,
at least one imaging system 20a, 20b, 20c, and
at least one first marker 70a, 70b, 70c that is arranged stationarily relative to the imaging system 20a, 20b, 20c as a reference marker, and the position and orientation of which are calibrated in a coordinate system 60a, 60b, 60c of the imaging system 20a, 20b, 20c as is also illustrated below in FIGS. 2a-2c.

FIGS. 2a, 2b and 2c schematically show an arrangement of several imaging systems with associated coordinate systems analogous to FIG. 1, wherein in FIGS. 2a, 2b and 2c, the same object 40 is examined in each case with a first marker 70a, 70b, 70c in different imaging or therapy modalities 20a, 20b, 20c.

In accordance therewith, each of a plurality of markers 70a, 70b, 70c is arranged in imaging systems 20a e.g. for MRT, 20b e.g. for CT, and 20c e.g. for IMRT but also PET such that their positions and orientations in the coordinate systems 60a, 60b, 60c of the respective imaging system 20a, 20b, 20c have been calibrated, wherein the position and orientation of the object marker 30 can be transferred from the coordinate system 60a of the imaging system 20a to the coordinate systems 60b and/or 60c of the imaging systems 20b and/or 20c.

The second marker 30 is advantageously mounted for arrangement on the movable object 40 such that the position and orientation of the marker 30 in the coordinate system 50 of the tracking system 10 can be detected during imaging and can be transferred to or be converted into the coordinate system 60a, 60b, 60c of the imaging system 20a, 20b, 20c.

The first marker 70a, 70b, 70c thereby cooperates with the tracking system 10 in such a fashion that a changing position of the tracking system 10 during imaging can be detected via the tracking system 10 by means of the first marker 70a, 70b, 70c and the tracking system 10 can be re-calibrated.

The tracking system 10 can thereby be arranged within or outside of the imaging system 20a, 20b, 20c.

The first marker 70a, 70b, 70c can also be arranged within or outside of the imaging system 20a, 20b, 20c.

Each of a plurality of markers 70a, 70b, 70c are arranged in respective imaging systems 20a, 20b, 20c such that their positions and orientations in the coordinate system 60a, 60b, 60c of the respective imaging system 20a, 20b, 20c are calibrated, wherein the position and orientation of the marker 30 arranged on the movable object 40 can be converted from the coordinate system 60a of the imaging system 20a into the coordinate systems 60b, 60c of the imaging systems 20b, 20c.

In each case, the imaging modality is naturally a different one, e.g. MRT, CT, IMRT, PET, SPECT and the like, wherein the reference marker is a different one in each case, since it is permanently connected to the imaging device. The tracking system may also be a different one or the same and be mobile or be stationary within or outside of the imaging system.

LITERATURE

1) Thesen S, Heid O, Mueller E, Schad L R. Prospective acquisition correction for head motion with image-based tracking for real-time fMRI. Magn Reson Med 2000; 44:457-465.
2) van der Kouwe A J, Benner T, Dale A M. Real-time rigid body motion correction and shimming using cloverleaf navigators. Magn Reson Med 2006; 56:1019-1032.
3) Ooi M B, Krueger S, Thomas W J, Swaminathan S V, Brown T R. Prospective real-time correction for arbitrary head motion using active markers. Magn Reson Med 2009; 62:943-954.
4) Dold C, Zaitsev M, Speck O, Firle E A, Hennig J, Sakas G. Prospective head motion compensation for MRI by updating the gradients and radio frequency during data acquisition. Med Image ComputAssist Interv 2005; 8 (Pt 1):482-489.
5) Zaitsev M, Dold C, Sakas G, Hennig J, Speck O. Magnetic resonance imaging of freely moving objects: prospective real-time motion correction using an external optical motion tracking system. Neuroimage 2006; 31:1038-1050.
6) Quin L, van Gelderen P, Derbyshire J A, Jin F, Lee J, de Zwart J A, Tao Y, Duyn J H. Prospective head-movement correction for highresolution MRI using an in-bore optical tracking system. Magn Reson Med 2009; 62:924-934.
7) B. C. Andrews-Shigaki, B. S. R. Armstrong, M. Zaitsev, et al., "Prospective Motion Correction for Magnetic Resonance Spectroscopy Using Single Camera Retro-Grate Reflector Optical Tracking", Journal of Magnetic Resonance Imaging, vol. 33, pp. 498-504, 2011
8) Aksoy M, Forman C, Straka M, Skare S, Holdsworth S, Hornegger J, Bammer R. Real time optical motion correction for diffusion tensor imaging. Magn Reson Med 2010; 66:366-378.
9) Forman C, Aksoy M, Hornegger J, Bammer R. Self-encoded marker for optical prospective head motion correction in MRI. Med Image Comput Comput Assist Interv 2010; 13 (Pt 1):259-266.
10) Aksoy M, Forman C, Straka M, Cukur T, Hornegger J, Bammer R.; Hybrid prospective and retrospective head motion correction to mitigate cross-calibration errors. Magn Reson Med. 2012 May; 67(5):1237-51. doi: 10.1002/mm.23101. Epub 2011 Aug. 8.
11) Boegle R, Maclaren J, Zaitsev M. Combining prospective motion correction and distortion correction for EPI: towards a comprehensive correction of motion and susceptibility-induced artifacts. MAGMA 2010; 23:263-273.
12) I. Kadashevich, D. Appu, O. Speck: "Automatic motion selection in one step cross-calibration for prospective MR motion correction". In: Proceedings of 28th Annual Scientific meeting of ESMRMB 2011. DOI:10.1007/s10334-011-0269
13) Hamilton, William Rowan, "On quaternions, or on a new system of imaginaries in algebra", Philosophical Magazine, vol. 25, pp. 489-495, 1844.

We claim:

1. A method for calibrating tracking systems in imaging systems and for prospective motion correction of a moving object being imaged or of a moving object being imaged in MRT, in IMRT or in CT, the method comprising the steps of:
   a) providing a tracking system having a tracking coordinate system;
   b) providing at least one imaging system having an imaging coordinate system;
   c) providing at least one first marker that is stationary relative to the imaging system as a reference marker having a position and orientation;
   d) cross calibrating the tracking coordinate system and the imaging coordinate system;
   e) measuring a position and orientation of the first marker in the tracking coordinate system;
   f) calibrating the position and orientation of the first marker in the imaging coordinate system;
   g) monitoring a position and orientation of the first marker in the tracking coordinate system;
   h) correcting the cross calibration of step d) using the results of step g), wherein the correction in the cross calibration is carried out using quaternion algebra;
   i) disposing at least one second marker on the moving object;
   j) detecting a position and orientation of the second marker in the tracking system coordinate system during imaging;
   k) converting, following step h), the position and orientation of the second marker detected in step j) into the coordinate system of the imaging system using quaternion algebra; and
   l) performing, following steps g) through k), a prospective motion correction such that an imaging volume remains stationary with respect to the moving object during imaging.

2. The method of claim 1, wherein said tracking system is arranged within said imaging system.

3. The method of claim 1, wherein said tracking system is arranged outside of said imaging system.

4. The method of claim 1, wherein said first marker is arranged within said imaging system.

5. The method of claim 1, wherein said first marker is arranged outside of said Imaging system.

6. The method of claim 1, wherein each of a plurality of markers is arranged in imaging systems such that positions and orientations thereof in a coordinate system of a respective imaging system are calibrated, wherein a position and orientation of the second marker arranged on the movable object is converted from a coordinate system of one imaging system into coordinate systems of other imaging systems.

7. The method of claim 1, wherein calibration is performed once as a cross calibration of the coordinate system of the tracking system with coordinates $c_0$ and C, wherein $c_0$ is the translation quaternion of the tracking system and C is a rotation quaternion of the tracking system and a position and orientation ($r_0$, R) of the first marker in the coordinate system of the tracking system are stored and a current position and orientation ($x_0$, X) of the reference point in the coordinate system of the tracking system is used for calibration in order to calculate a current cross calibration ($s_0$, S) as follows:

$$S = X^* RC,$$

wherein $X^*$ is a conjugated rotation quaternion of a quaternion X and $$s_0 = c_0 + C^* r_0 C - S^* x_0 S,$$

wherein $C^*$ and $S^*$ are conjugates of rotation quaternions C and S.

8. A method for calibrating tracking systems in an imaging apparatus and for prospective or for retrospective motion correction of a moving object being imaged by the imaging apparatus or of a moving object being imaged in MRT, in IMRT or in CT, the method comprising the steps of:
 a) providing a tracking system having a tracking coordinate system;
 b) providing at least one imaging system having an imaging coordinate system;
 c) providing at least one first marker that Is stationary relative to the imaging system as a reference marker having a position and orientation;
 d) cross calibrating the tracking coordinate system and the imaging coordinate system;
 e) measuring a position and orientation of the first marker in the tracking coordinate system;
 f) calibrating the position and orientation of the first marker in the imaging coordinate system;
 g) removing the tracking system from the imaging apparatus;
 h) reinstalling the tracking system in the imaging apparatus;
 i) measuring a position and orientation of the first marker in the tracking coordinate system following step h);
 j) correcting the cross calibration of step d) using the results of step i), wherein the correction in the cross calibration is carried out using quaternion algebra;
 k) disposing at least one second marker on the moving object;
 l) detecting a position and orientation of the second marker in the tracking system coordinate system during imaging;
 m) converting, following step j), the position and orientation of the second marker detected in step l) into the coordinate system of the imaging system using quaternion algebra; and
 n) performing, following steps i) through m), a prospective or a retrospective motion correction such that an imaging volume remains stationary with respect to the moving object.

9. The method of claim 8, wherein said tracking system is arranged within said imaging system.

10. The method of claim 8, wherein said tracking system is arranged outside of said imaging system.

11. The method of claim 8, wherein said first marker is arranged within said imaging system.

12. The method of claim 8, wherein said first marker is arranged outside of said imaging system.

13. The device of claim 8, wherein each of a plurality of markers is arranged in imaging systems such that positions and orientations thereof are calibrated in a coordinate system of a respective imaging system, wherein a position and orientation of a marker arranged on a movable object is transferred from a coordinate system of an imaging system to coordinate systems of other imaging systems through measurement of position and orientation using said tracking system.

14. The method of claim 8, wherein calibration Is performed once as a cross calibration of the coordinate system of the tracking system with coordinates $c_0$ and C, wherein $c_0$ is the translation quaternion of the tracking system and C is a rotation quaternion of the tracking system and a position and orientation ($r_0$, R) of the first marker in the coordinate system of the tracking system are stored and a current position and orientation ($x_0$, X) of the reference point in the coordinate system of the tracking system is used for calibration in order to calculate a current cross calibration ($s_0$, S) as follows:

$$S = X^* RC,$$

wherein $X^*$ is a conjugated rotation quaternion of a quaternion X and $$s_0 = c_0 + C^* r_0 C - S^* x_0 S,$$

wherein $C^*$ and $S^*$ are conjugates of rotation quaternions C and S.

* * * * *